United States Patent [19]

Reagen et al.

[11] Patent Number: 5,994,604
[45] Date of Patent: *Nov. 30, 1999

[54] METHOD AND APPARATUS FOR LOW TEMPERATURE DESTRUCTION OF HALOGENATED HYDROCARBONS

[75] Inventors: William Kevin Reagen, Stillwater, Minn.; Stuart Kevin Janikowski, Idaho Falls, Id.

[73] Assignee: Lockheed Martin Idaho Technologies Company, Idaho Falls, Id.

[ * ] Notice: This patent issued on a continued prosecution application filed under 37 CFR 1.53(d), and is subject to the twenty year patent term provisions of 35 U.S.C. 154(a)(2).

[21] Appl. No.: 08/568,442

[22] Filed: Dec. 7, 1995

Related U.S. Application Data

[63] Continuation-in-part of application No. 08/327,342, Oct. 21, 1994, abandoned, which is a continuation of application No. 08/032,937, Mar. 17, 1993, abandoned.

[51] Int. Cl.[6] .............................. C07C 1/26; C01B 7/01; C01B 9/00
[52] U.S. Cl. .................. 585/469; 208/262.1; 208/262.5; 423/481; 423/491; 585/638; 585/733
[58] Field of Search .............................. 208/262.1, 262.5; 423/481, 491; 585/469, 638, 733

[56] References Cited

U.S. PATENT DOCUMENTS

| | | |
|---|---|---|
| 4,351,978 | 9/1982 | Hatano et al. . |
| 4,806,514 | 2/1989 | Langford et al. . |
| 4,931,167 | 6/1990 | Wilwerding . |
| 4,950,833 | 8/1990 | Hawari et al. ........................... 585/469 |
| 5,043,054 | 8/1991 | Halpern et al. .......................... 585/733 |
| 5,141,629 | 8/1992 | Pri-Bar et al. .......................... 585/469 |
| 5,174,893 | 12/1992 | Halpern et al. ........................ 585/733 |
| 5,185,488 | 2/1993 | Hawari et al. ........................... 585/469 |
| 5,490,919 | 2/1996 | Pri-Bar et al. ........................ 208/262.1 |

OTHER PUBLICATIONS

Analysis of Polychlorinated Naphthalenes, Polychlorinated Biphenyls & Polychlorinated Terphenyls via Cargon Skeleton Gas–Liquid Chromatograph, by Michael Cooke et al., J. of Chromatography, vol. 156, pp. 293–299 (1978) no month available.

Column Chromatographic Separation of Polychlorinated Biphenyls from Chlorinated Hydrocarbon Pesticides, and their Subsequent Gas Chromatographic Quantitation in Terms of Derivatives, by O.W. Berg et al., Bulletin of Environmental Contamination and Toxicology, vol. 7, No. 6, (1972). no month available.

*Primary Examiner*—Elizabeth D Wood
*Attorney, Agent, or Firm*—W. Gary Goodson

[57] ABSTRACT

A method and apparatus for decomposing halogenated hydrocarbons are provided. The halogenated hydrocarbon is mixed with solvating agents and maintained in a predetermined atmosphere and at a predetermined temperature. The mixture is contacted with recyclable reactive material for chemically reacting with the recyclable material to create dehalogenated hydrocarbons and halogenated inorganic compounds. A feature of the invention is that the process enables low temperature destruction of halogenated hydrocarbons.

18 Claims, 1 Drawing Sheet

METHOD AND APPARATUS FOR LOW TEMPERATURE DESTRUCTION OF HALOGENATED HYDROCARBONS

This is a continuation-in-part of application Ser. No. 08/327,342, filed Oct. 21, 1994, now abandoned, which is a continuation of prior application Ser. No. 08/032,937 filed Mar. 17, 1993, now abandoned.

CONTRACTUAL ORIGIN OF THE INVENTION

The United States Government has rights in this invention pursuant to Contract No. DE-AC07-76ID01570 between the United States Department of Energy and EG&G Idaho, Inc., now Contract No. DE-AC07-94ID13223 between the U.S. Department of Energy and Lockheed Idaho Technologies Company. the operator of the Idaho National Engineering Laboratory.

BACKGROUND OF THE INVENTION

1. Field of the Invention

The present invention relates generally to apparatus and a method for decomposing halogenated compounds, and more specifically to apparatus and a method for the low temperature destruction of halogenated hydrocarbons.

2. Background of the Invention

The persistence of halogenated compounds in the environment continues to pose ecological and health problems. These compounds are of both the aliphatic and aromatic variety and are associated with aspects of electronic component fabrication, dielectric applications, metal finishing industries, paint production, plastics production/recycling, oil production industries, and other industrial applications. Such compounds include the polyhalogenated aromatic- and polyaromatic-compounds (e.g., the polychlorinated biphenyls) and the alkyl halides (e.g., polyhalogenated ethylene, chloroform, carbon tetrachloride, methylene chloride, and others).

A myriad of disposal techniques have been studied in attempts to degrade or otherwise isolate these compounds, including burial, incineration, photodecomposition, adsorption, and chemical degradation. Generally, methods to degrade halogenated materials into innocuous products have had limited success due to stringent operating parameters associated with those methods. For example, the addition of alkaline solutions into a mixture containing polychlorinated biphenyls (PCBs) with alcohol dispersing agents, has been attempted to decompose halogenated material (U.S. Pat. No. 4,351,978). This technique, which utilizes Raney catalysts, requires establishing and maintaining alkaline conditions so as to maintain the reactive capabilities of the catalyst. The technique also requires the addition of gaseous hydrogen to effect substitution of the halogen moieties. Another process (U.S. Pat. No. 4,931,167) requires the use of Lewis acid catalysts in anhydrous conditions, and at temperatures in excess of 300° C.

Thermal degradation is the method allowed by the U.S. Environmental Protection Agency for fluids which contain more than 500 parts per million (ppm) polychlorobiphenyls (PCBs). However, much criticism has been directed towards thermal incineration as an uneconomical means of destroying these materials. The many shortcomings of utilizing typical incineration methods include high capital costs of constructing large-bed reaction zones, and the high operating costs of maintaining molten salt systems and incineration systems at 1100° C. and 2600° C., respectively. The need for large beds and long residence times to effect conversion of halogenated materials to innocuous salts or gaseous decomposition products is directly related to the high costs of these processes. Limited incinerators currently exist for disposing of halogenated waste so that toxic chemicals must be stockpiled prior to disposal.

A need exists in the art for a low cost, highly efficient alternative technology to conventional halogenated hydrocarbon incineration. Such technology should operate at relatively lower temperatures, be able to economically dispose of hazardous waste, and use recyclable reaction materials. Also, these recyclable materials should be commercially available. Such a system would ameliorate the problems and costs associated with stockpiling halogenated waste material and would also facilitate bench-top disposal capability so as to allow disposal of toxics where they are normally produced, used, or discarded.

SUMMARY OF THE INVENTION

It is an object of the present invention to provide apparatus and a method for decomposing halogenated hydrocarbons that overcomes many of the disadvantages of the prior art.

It is another object of the present invention to provide a method for decomposing halogenated hydrocarbons that utilizes low temperatures and is low cost.

It is yet another object of the present invention to provide a method for dehalogenating polyhalogenated compounds utilizing catalysts that provide high efficiency conversion of the polyhalogenated compounds to dehalogenated compounds using less hazardous, less costly materials which are recyclable, and which is carried out in the absence of an alkali metal hydroxide unlike prior art methods.

Still another object of the present invention is to provide a method for degrading halogenated hydrocarbons to non-halogenated organic compounds and salts providing improved efficiencies and reduction of prior art incineration costs associated with degrading halogenated aromatic, polyaromatic and aliphatic compounds.

In brief, these and other objects of the invention are achieved by a method and apparatus for decomposing a halogenated hydrocarbon. The halogenated hydrocarbon is mixed with solvating agents and maintained in a predetermined atmosphere and at a predetermined temperature.

The mixture is contacted with recyclable reactive material for chemically reacting with the recyclable material to create dehalogenated hydrocarbons and halogenated inorganic compounds. A feature of the invention is that the process enables low temperature destruction of halogenated hydrocarbons.

BRIEF DESCRIPTION OF THE DRAWING

The present invention, together with the above and other objects and advantages, may best be understood from the following detailed description of the embodiment of the invention illustrated in the drawing, wherein.

DETAILED DESCRIPTION OF THE INVENTION

Figure 1:
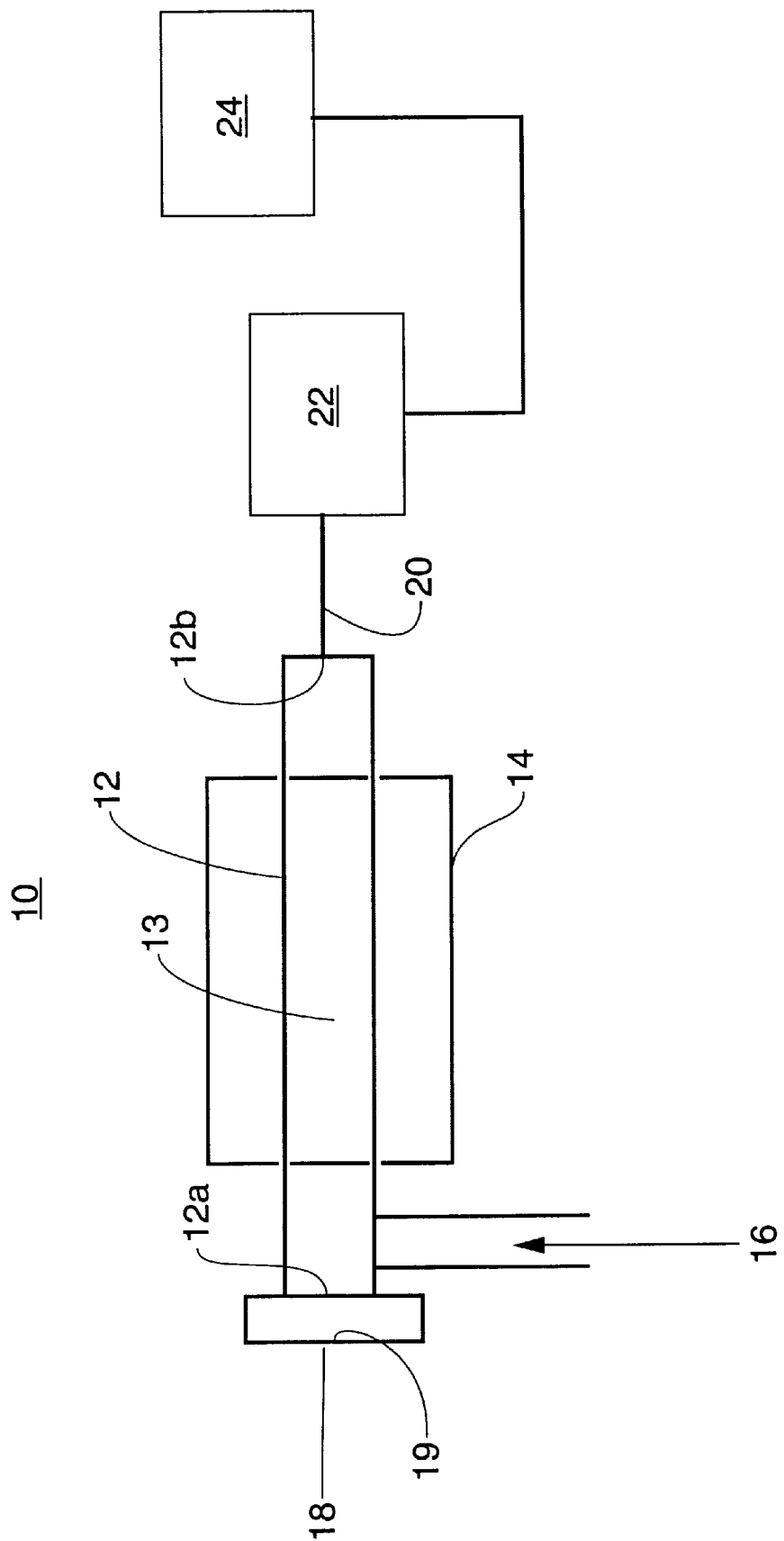
FIG. 1 is a schematic diagram of an exemplary apparatus for carrying out the low temperature destruction of halogenated compound process of the present invention.

Referring to the drawing, there is shown an apparatus generally designated by reference character 10 that can be used for carrying out the process of the present invention. It has been found that a decomposition method using supported metal catalysts, unsupported metal catalysts, inorganic oxides, metal salts or mixtures of these materials exhibit conversion of halogenated compounds at low temperatures, while using less hazardous and less costly commercially available materials. The process services a wide range of hazardous halogenated compound destruction and conversion applications and eliminates the need for dihydrogen as a required reagent.

Surprisingly and unexpectedly, the inventors have achieved quantitative conversions of halogenated aromatic and aliphatic compounds at temperatures of approximately 180° C. This development confers great advantages over typical incineration systems which require temperatures in excess of 1100° C. The process enables selective and aggressive conversion of halogenated hydrocarbons without degrading the salt/catalyst materials, or the solvating reagents.

Generally, a feedstream including halogenated hydrocarbons 18 is routed via an inlet port 19 to a closed reaction chamber generally designated as 12 having an inlet 12a and an outlet 12b which contains catalyst material or inorganic oxides generally designated as 13. Depending on the reaction products desired, certain solvating agents are combined with the feedstream before, during or after the feedstream is routed to the closed reaction chamber 12.

The catalyst bed temperatures in the reaction chamber 12 were varied with a heating mechanism or tube furnace 14 to a predetermined range between 180° C. and 350° C. An air, inert, or air/inert atmosphere is effected with a gas flow inlet 16 for supplying air or inert gas to the reaction chamber 12. The treated feedstream flows through a conduit for collection by a solvent trap 22. Trap 22 could be a cold trap to isolate liquid organics, activated carbon to isolate gases, a typical NaOH scrubber to neutralize the acids formed in the redox reaction or some other device, depending on the product expected.

Product collection materials can be analyzed via quantitative and qualitative analysis indicated at block 24. Gas chromatography mass spectroscopy, wet bench analysis or a combination of analytical techniques can be employed.

This process of dehalogenating halogenated compounds exploits the affinity that alkyl moieties (from the solvating agents contained in the reaction mixture) have for the electrophilic centers of unsaturated systems. As such, conversions are effected at low temperatures ranging from 150° C. to 400° C.

Feedstream Detail

The classes of halogenated hydrocarbons that can be treated with the invented process include the halogenated aromatics, the halogenated polyaromatics and the halogenated aliphatics. These feedstreams can be in a variety of forms, including neat or diluted solutions or hydrocarbon solutions. The feedstreams can also be treated regardless of phase. For example, liquid feedstreams can be injected directly into the reaction chamber or vaporized by combining with heated carrier gas that is introduced to the closed reaction chamber via the injection port 16. All types of halogens can be substituted including fluorine, chlorine, bromine and iodine.

As is depicted in Equations I–VIII below, the invented process has effected complete conversion of the chlorinated hydrocarbons p-dichlorobenzene, orthochlorophenol, 2-chloro-1,1-biphenyl and 1,1-dichloroethane. These materials were reacted with catalyst beds as neat samples, alcohol solutions and hydrocarbon solutions.

Heating Detail

The heating mechanism 14 is utilized to attain and maintain the catalyst bed 13 in the reaction chamber at a predetermined temperature. The heating mechanism 14 can include an external element, such as a flame impinging on the sides of the closed reaction vessel chamber 12, an internal element, or a heated carrier gas which can be introduced into the reaction chamber 12 via the gas flow inlet 16. Whether or not heated carrier gas is utilized, the gas flow inlet 16 is situated at the upstream end 12a of the reaction chamber to facilitate fluid flow through the chamber.

Recyclable Reactive Material Detail

A variety of different catalysts and oxides can be utilized and selected from the group consisting of metal salts, inorganic oxides, supported metals, unsupported metals, or combinations of these materials.

Supported or unsupported metals which can be utilized as catalysts in the decomposition reaction can be found in Group VIII of the periodic table and are selected from the metals group consisting of platinum, nickel, palladium, cobalt, rhodium, iridium, or combinations thereof. In addition, the metals, copper and zinc can be selected for use as the catalyst.

A supported metal is defined as a metal being attached or as a coating on the alumina ($Al_2O_3$) carrier and an unsupported metal is defined as only the metal without the $Al_2O_3$ carrier. Unsupported metals used as catalysts can be selected from the group consisting of Zn, Cu, Ni, Co, Fe, Pt, Pd, and combinations thereof. Supported metals and their supporting compounds can be selected from the group consisting of $Pt/Al_2O_3$, $Ni/Al_2O_3$, $Pd/Al_2O_3$, $Co/Al_2O_3$, $Rh/Al_2O_3$, $Ir/Al_2O_3$ and combinations thereof. Extensive tests using platinum supported on alumina as catalyst ($Pt/Al_2O_3$) exhibits complete conversion of halogenated hydrocarbons to their respective hydrogenation products at 180° C. and to a variety of alkylated products and ring systems at 350° C.

Inorganic oxides typically utilized in the process include $TiO_2$, $MnO_2$, $Fe_2O_3$, $SiO_2$, $La_2O_3$, and combinations thereof. $MnO_2$ salt bed systems exhibit complete conversion of halogenated hydrocarbons and non-halogenated to $CO_2$ at temperatures less than 350° C. to over 400° C.

Generally, the invention utilizes very small loadings of metal catalysts on substrates, thereby enhancing the feature of economy. For example, a 0.5–1 percent (weight) loading of platinum on ($Al_2O_3$) provided good results in the dehalogenation of halogenated aromatics at low temperatures and in the absence of dihydrogen. When higher amounts of a catalyst are used, the residence time of the halogenated substrate in the reactor decreases with a concomitant high turnover rate to dehalogenated products.

The disposition of the catalyst material or oxidation material can vary within the reaction chamber.

While good results have been obtained by merely placing these materials within the reaction chamber 12, other configurations are equally viable, including supporting the catalyst material on glass, or impregnating the material into a fiber matrix or a zeolite cake. In fact, supporting the catalysts will alleviate liquid accumulation which often occurs when heating hygroscopic, powdered materials to the 100°–400° C. temperature range. Liquid accumulation can also be alleviated by mixing sand into powdered formulations of inorganic oxides. Fluidized bed configurations will further enhance the redox efficiencies associated with these oxides.

A salient feature of the process is the ability to regenerate the catalyst or oxide through high temperature cycling in an oxidizing atmosphere. For example, after reacting, the now-reduced manganese in the form of its halogen salt can be oxidized back up to $MnO_2$, in a classic reversal of the foregoing redox reaction with the halogenated substrate.

Metal catalysts, either supported or unsupported, experience impurity build-up or fouling after initial use. Such detriments are reversed to provide nearly virgin catalytic efficiencies via treatment in heated air. Surprisingly and unexpectedly, it was observed that after initial cycling of metal catalysts, the efficiency of the invented process remained patent. Some product redistribution was noted, however.

Solvating Agent Detail

A myriad of solvating agents can be utilized in conjunction with the catalysts, including alcohols and alkanes. Other solvating agents that can be utilized include the aromatics, toluene, ethylbenzene and combinations thereof. Regarding alcohols, both the lower and high chain alcohols are applicable, including methanol, ethanol, propanol, butanol and hexanol. It was found that when longer length alcohols are utilized, the system behaves as if the corresponding alkane, such as hexane, was utilized.

Alkanes are particularly good reagents for the invented process. With longer chain reagents, more complete substitution of halogenated compounds occurs. For example, hexane's four methylene groups and two methyl groups provide six carbons as substitution moieties. The efficiency of this system is depicted in Equation III, below wherein hexamethylbenzene was formulated when hexane was combined with platinum catalyst.

Some of the alcoholic and aliphatic reagents are consumed in the process in stoichiometric quantities, proportional to the concentration of the reacting halides.

As such, the ratios between the halogenated substrate and within a certain class of reagent solvents effect the product yields in the reaction. For example, with a 1:1 stoichiometric ratio of halogen with hydroxyl moiety, a one-to-one displacement on the halogenated aromatic is predominant. However, a surplus of hydroxyl will result in more substitution.

Substitution does not always result in the same moieties being attached. In some instances, the halogen is substituted for a hydrogen, or an alkyl, or an alkoxy group. When, for example, methanol is used as a reagent, hydrogen, a methyl or a methoxy group substitutes for the halogen.

Atmosphere Detail

A variety of non-reactive atmospheres can be utilized in the invention, depending on the products desired. For example, the noble gases helium, argon, neon, krypton, zenon, radon, or combinations thereof, are good choices for creating a non-reactive atmosphere in the present invention. Mixtures of these inert gases with air, nitrogen or even hydrogen may be desirable to facilitate halocarbon degradation and/or dehalogenation. Additionally, a nitrogen atmosphere can be used in the present invention.

The high efficiency, low cost of the invention is partially due to the required pressures of the gases, out-lined above, being very low with typical pressures ranging from ambient to 30 psi. However, pressures as high as 100 atm would not effect the efficiency of the invented process or apparatus.

Temperature Detail

Relatively low temperatures are utilized in the process so as to maintain the technical efficiency and therefore the economical nature of the invention. A reaction chamber temperature selected from a range of approximately 100° C. to 400° C. is typical, but the invention is not bounded by these temperatures. In fact, reaction temperatures can vary widely, as long as fusing point temperatures of the silica/alumina supports are not attained.

As noted above, product types and yields directly depend on the reagents and catalysts used in the reaction. Within a catalyst category, product yields also differ, depending on temperature and the reagents used. In equations I–VI below, a myriad of reaction products are obtained when the catalyst type, $Pt/Al_2O_3$, remains constant, and the reagents and temperatures are changed.

EQUATION I

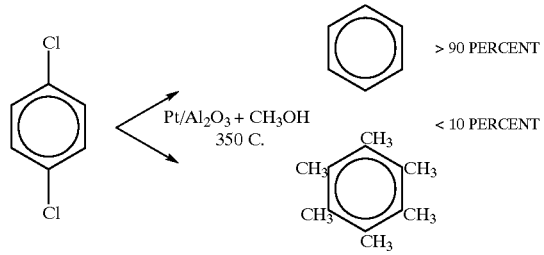

EQUATION II

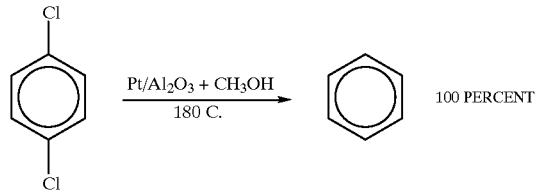

-continued

EQUATION III

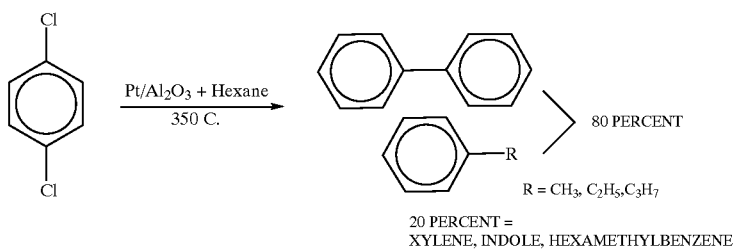

EQUATION IV

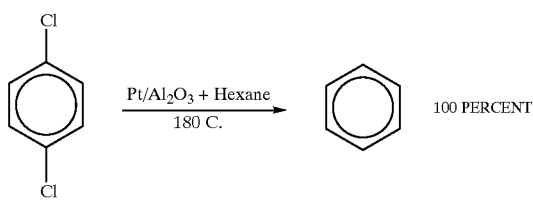

EQUATION V

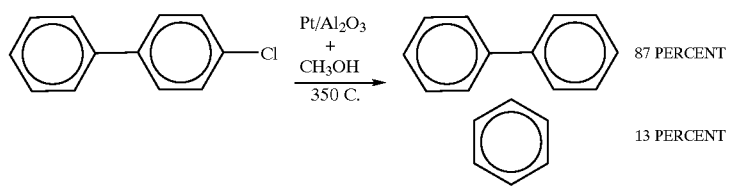

EQUATION VI

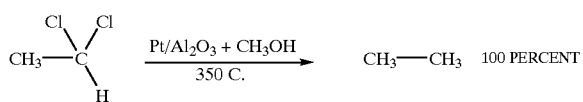

Generally, the platinum supported catalyst systems exhibit complete conversion of halogenated hydrocarbons to the respective hydrogenation products at 180° C. and to a variety of alkylated products and ring systems at 350° C.

As is demonstrated in equations VII and VIII, $MnO_2$ salt bed systems exhibit complete conversion of halogenated hydrocarbons to $CO_2$ at temperatures ranging from less than 300° C. to over 400° C.

EQUATION VII

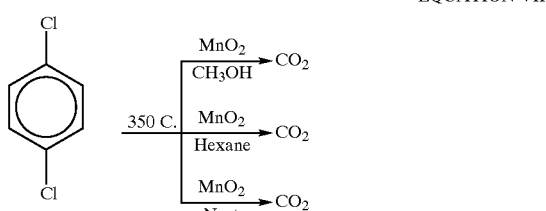

EQUATION VIII

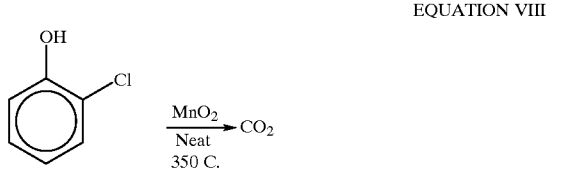

Prudence dictates that due to the exothermic nature of the bond cleavage associated with this oxidizer, the rate of introduction of halogenated substrate into the reaction chamber 12 containing $MnO_2$ should be relatively slow. Such a precaution will ensure higher production of the associated manganese salt while minimizing the formation of explosive mixtures.

While the invention has been described with reference to details of the illustrated embodiment, these details are not intended to limit the scope of the invention as defined in the appended claims.

The embodiment of the invention in which an exclusive property or privilege is claimed is defined as follows:

1. A method for decomposing a halogenated hydrocarbon comprising the steps of:
   a) mixing the halogenated hydrocarbon with a solvating agent selected from the group consisting of alcohols, alkanes, aromatics and combinations thereof;
   b) maintaining the mixture of step a) in an atmosphere non-reactive with the mixture and at a temperature from 180° to 350° C.; and
   c) contacting the mixture with a catalyst selected from the group consisting of a metal salt, an inorganic oxide, a supported metal and supporting compound, and unsupported metal, and combinations thereof for chemically reacting the mixture with the catalyst to create dehalogenated hydrocarbons and halogenated inorganic compounds, the method being conducted in the absence of an alkali metal hydroxide.

2. A method as recited in claim 1 further comprising the step of collecting the dehalogenated hydrocarbons and halogenated inorganic compounds.

3. The method as recited in claim 1 wherein the halogenated hydrocarbon is selected from a group consisting of halogenated aromatic compounds, halogenated polyaromatic compounds, halogenated aliphatic compounds, and combinations thereof.

4. The method of claim 1 wherein the non-reactive atmosphere consists of a gas selected from the group consisting of helium, nitrogen, argon, neon, krypton, xenon, radon, and combinations thereof and wherein said non-reactive atmosphere and mixture of step a) are at a pressure of no more than about 1 to 3 atmospheres.

5. The method as recited in claim 1 wherein the catalyst is an inorganic oxide selected from the group consisting of $TiO_2$, $MnO_2$, $Fe_2O_3$, $Al_2O_3$, $SiO_2$, $La_2O_3$, and combinations thereof.

6. The method as recited in claim 1 wherein the catalyst includes the supported metal and supporting compound $PT/Al_2O_3$.

7. The method in claim 1 wherein the catalyst is an unsupported metal is selected from the group consisting of Zn, Cu, Ni, Co, Fe, Pt, Pd, and combinations thereof.

8. The method as recited in claim 1 wherein the solvating agent is an alcohol selected from the group consisting of methanol, ethanol, propanol, butanol, hexanol, and combinations thereof.

9. The method as recited in claim 1 wherein the solvating agent is an alkane selected from the group consisting of methane, ethane, propane, butane, pentane, hexane, and combinations thereof.

10. The method as recited in claim 1 wherein the solvating agent is an aromatic selected from the group consisting of toluene, ethylbenzene, and combinations thereof.

11. A method for dehalogenating a halogenated hydrocarbon comprising:
   a) mixing the halogenated hydrocarbon with a solvating agent including an alkane;
   b) maintaining the mixture of step a) in an atmosphere non-reactive with the mixture and at a temperature from 180° to 350° C.;
   c) contacting the mixture with a catalyst selected from the group consisting of a metal salt, an inorganic oxide, a supported metal and supporting compound, an unsupported metal, and combinations thereof for chemical reacting the mixture with the catalyst to create dehalogenated hydrocarbons and halogenated inorganic compounds, the method being conducted in the absence of an alkaline metal hydroxide
   d) collecting the dehalogenated hydrocarbons and halogenated inorganic compounds.

12. The method as recited in claim 11 wherein the halogenated hydrocarbon is selected from the group consisting of halogenated aromatic compounds, halogenated polyaromatic compounds, halogenated aliphatic compounds, and combinations thereof.

13. The method as recited in claim 11 wherein the inert atmosphere consists of an inert gas selected from the group consisting of helium, nitrogen, argon, neon, krypton, xenon, radon and combinations thereof.

14. The method as recited in claim 11 wherein the catalyst is an inorganic oxide selected from the group consisting of $TiO_2$, $MnO_2$, $Fe_2O_3$, $Al_2O_3$, $SiO_2$, $La_2O_3$, and combinations thereof.

15. The method as recited in claim 11 wherein the catalyst is the supported metal and supporting compound is $Pt/Al_2O_3$.

16. The method in claim 11 wherein the catalyst is an unsupported metal is selected from the group consisting of Zn, Cu, Ni, Co, Fe, Pt, Pd, and combinations thereof.

17. The method as recited in claim 1 wherein the solvating agent is an alkane selected from the group consisting of methane, ethane, propane, butane, pentane, hexane, and combinations thereof.

18. A method for dehalogenating a halogenated hydrocarbon comprising the steps of:
   a) mixing the halogenated hydrocarbon with an aromatic selected form the group consisting of toluene, ethylbenzene, and combinations thereof;
   b) maintaining the mixture of step a) in an inert gaseous atmosphere selected from the group consisting of helium, nitrogen, argon, neon, krypton, xenon, radon, and combinations thereof and at a temperature from 180° to 350° C.;
   c) contacting the mixture with a catalyst selected from the group consisting of $PT/Al_2O_3$, $Ni/Al_2O_3$, $Pd/Al_2O_3$, $Co/Al_2O_3$, $Rh/Al_2O_3$, $Ir/Al_2O_3$ and combinations thereof for chemically reacting with the catalyst to create dehalogenated hydrocarbons and halogenated inorganic compounds the method being carried out without the addition of alkaline solutions to the mixture; and
   d) collecting the dehalogenated hydrocarbons and halogenated inorganic compounds.

* * * * *